(12) United States Patent
Parsons et al.

(10) Patent No.: US 9,036,786 B2
(45) Date of Patent: May 19, 2015

(54) TRANSMISSION TYPE X-RAY TUBE AND REFLECTION TYPE X-RAY TUBE

(75) Inventors: Bruce Briant Parsons, New Taipei (TW); Chi-Chieh Cheng, New Taipei (TW)

(73) Assignee: NanoRay Biotech Co., Ltd., New Taipei (TW)

( * ) Notice: Subject to any disclaimer, the term of this patent is extended or adjusted under 35 U.S.C. 154(b) by 259 days.

(21) Appl. No.: 13/489,446

(22) Filed: Jun. 5, 2012

(65) Prior Publication Data

US 2013/0108024 A1 May 2, 2013

(30) Foreign Application Priority Data

Oct. 28, 2011 (TW) .............................. 100139390 A

(51) Int. Cl.
| | |
|---|---|
| *H01J 35/00* | (2006.01) |
| *H01J 35/02* | (2006.01) |
| *H01J 35/08* | (2006.01) |
| *G21K 3/00* | (2006.01) |
| *H01J 35/18* | (2006.01) |
| *A61B 6/00* | (2006.01) |

(52) U.S. Cl.
CPC ................. *H01J 35/08* (2013.01); *H01J 35/18* (2013.01); *H01J 2235/081* (2013.01); *H01J 2235/087* (2013.01); *H01J 2235/186* (2013.01); *A61B 6/508* (2013.01)

(58) Field of Classification Search
CPC ........... H01J 35/00; H01J 35/02; H01J 35/08; H01J 35/12; H01J 35/18; H05G 1/00; G01J 5/0862; G21K 1/00; G21K 1/10; G02B 5/20; G02B 5/22; G02B 7/006; G02B 27/0938; G01N 2021/6471

USPC ......... 378/119, 121, 125–139, 140, 143, 144, 378/204, 210, 156; 250/423 R, 424, 427, 250/493.1, 503.1, 526

See application file for complete search history.

(56) References Cited

U.S. PATENT DOCUMENTS 3,515,874 A * 6/1970 Bens et al. ...................... 378/37
5,365,567 A * 11/1994 Ohtsuchi et al. ............... 378/156

(Continued)

FOREIGN PATENT DOCUMENTS

| CN | 1252618 | 5/2000 |
|---|---|---|
| CN | 1453817 | 11/2003 |

(Continued)

OTHER PUBLICATIONS

"Office Action of Taiwan Counterpart Application", issued on May 23, 2014, p. 1-p. 7.

(Continued)

*Primary Examiner* — Anastasia Midkiff
(74) *Attorney, Agent, or Firm* — Jianq Chyun IP Office

(57) ABSTRACT

The present invention provides a transmission type X-ray tube and a reflection type X-ray tube. The transmission type X-ray tube comprises a target and a filter material. The target has at least one element which produces X-rays as being excited. The X-rays comprise characteristic Kα and Kβ emission energies of the element for producing images of an object impinged by the X-rays. The filter material through which the X-rays pass has a k-edge absorption energy that is higher than the Kα emission energies and is lower than the Kβ emission energies. The thickness of the filter material is at least 10 microns and less than 3 millimeters.

6 Claims, 9 Drawing Sheets

(56) References Cited

U.S. PATENT DOCUMENTS

| | | | | |
|---|---|---|---|---|
| 5,375,158 | A | * | 12/1994 | Logan .................. 378/143 |
| 7,203,283 | B1 | | 4/2007 | Puusaari |
| 2004/0109536 | A1 | | 6/2004 | Shefer et al. |
| 2005/0123097 | A1 | * | 6/2005 | Wang .................. 378/143 |
| 2008/0267348 | A1 | * | 10/2008 | Puusaari et al. ........ 378/44 |
| 2010/0020934 | A1 | * | 1/2010 | Morton ................ 378/124 |

FOREIGN PATENT DOCUMENTS

| | | |
|---|---|---|
| CN | 101310359 | 11/2008 |
| DE | 3716618 | 12/1988 |
| JP | H02-104564 | 8/1990 |
| JP | 2001190531 | 7/2001 |
| JP | 2003505845 | 2/2003 |
| JP | 2007-207539 | 8/2007 |
| JP | 2008-268105 | 11/2008 |
| JP | 2008268105 | 11/2008 |
| TW | 201101363 | 1/2011 |
| WO | 2008078477 | 7/2008 |

OTHER PUBLICATIONS

"Office Action of Germany Counterpart Application", issued on Aug. 26, 2013, p. 1-p. 8.

"Office Action of Japan Counterpart Application", issued on Nov. 19, 2013, p. 1-p. 3.

Yinghua Wang, "Basis of X-ray Diffraction Technology," Trial Textbook for Institutions of Higher Education, Apr. 1987, pp. 1-22.

"Office Action of China Counterpart Application", issued on Dec. 31, 2014, p1-p8.

"Office Action of Japan Counterpart Application", issued on Dec. 2, 2014, p1-p2.

* cited by examiner

2

TRANSMISSION TYPE X-RAY TUBE AND REFLECTION TYPE X-RAY TUBE

CROSS-REFERENCE TO RELATED APPLICATION

This application claims the priority benefit of Taiwan application serial no. 100139390, filed on Oct. 28, 2011. The entirety of the above-mentioned patent application is hereby incorporated by reference herein and made a part of this specification.

BACKGROUND OF THE INVENTION

1. Field of the Invention

The present invention generally relates to a transmission type X-ray tube and a reflection type X-ray tube. More particularly, the present invention relates to a transmission type X-ray tube and a reflection type X-ray tube using filter materials to filter out unwanted radiation.

2. Description of Related Art

It is well know in the art of medical imaging that by using low Z filters such as aluminum, molybdenum, yttrium and copper the amount of low energy radiation can be reduced by what is referred to an aluminum equivalent filter thickness. Typically such thickness would range from 0.5 to 12 millimeters of equivalent aluminum filter which filters out x-rays of low energy, long wavelength, reducing potentially harmful and unnecessary radiation especially for medical imaging. Unfortunately such filters also filter out a large portion of the useful x-rays.

Non-destructive testing usually does not employ filters but when imaging of a specific Kα line emission from the target of the x-ray tube provides a high quality image of the object to be imaged in non-destructive testing, removal of unwanted high energy photons which cause loss of energy quality is also an objective of the current invention.

In medical imaging chemical imaging agents, such as iodine, gadolinium and barium based compounds, produce high contrast with respect to surrounding soft tissue because of their densities and atomic numbers. The significance of their atomic numbers (Z=53 for iodine, Z=56 for barium and Z=64 for gadolinium) is that the k-absorption edge is located at very favorable energies relative to the typical x-ray energy spectrum. The K edge for iodine is at 33.17 keV, is at 37.44 keV for barium and is at 50.24 kev for gadolinium). Maximum contrast is produced when the x-ray photon energy is slightly above the K-edge energy of the chemical imaging agents.

The selection of an optimum spectrum for a specific clinical procedure must take into consideration not only the requirements for contrast but also produce the necessary penetration through the body section and limit the radiation dose to the patient.

In the case of non-destructive imaging of various industrial products including but not limited to electronic circuit boards of all kinds, integrated circuits, LED's and lithium batteries, there is a single optimum energy for maximum image quality. However, in order to produce such a high flux optimum energy, inevitably higher energy photons above the optimum energy are produced at the same time. Such high energy photons are unwanted as they decrease image contrast. Sensor overload is a problem when too many x-rays not essential to making the image impinge on the sensor.

For a reflection type x-ray tube the spectrum of an x-ray beam is determined by combinations of the anode material, the filter material and thickness, and the selected electron tube voltage for the procedure. The thickness of the target is not a significant issue.

What is needed for x-ray imaging applications is an x-ray spectrum with a high number of photons in a narrow, well defined band of x-ray photon energies to provide high image contrast and a way to filter out those photons with energies higher and/or lower than the energy band while only minimally reducing the flux in said energy band is required to maximize image quality. The ratio of flux in the useful energy band to the energy above such band should be maximized within the limitations of thermal management of the x-ray tube. For medical imaging applications a way to simultaneously decrease the unnecessary low energy photons significantly reducing dose to the patient would provide a significant added benefit. For imaging of inanimate objects the photon energies can be as low as 15 to 20 kev while for general medical imaging would start closer to 30 kev and be as high as 600 kev for high energy imaging.

Such a filtering scheme is applicable to both reflection type and transmission type of x-ray tubes. When transmission tubes are used what is needed is way to optimize the ratio of useful x-rays to the amount of high energy photons above the useful x-ray band. In medical applications what is needed is a way to optimize the ratio of useful x-rays to the dose the patient receives while at the same time reducing the number of high energy photons above the useful band. Reflection tubes do not allow for optimization of flux using target thickness and hence are limited to adjusting the thickness and composition of the filter material to provide the same desired results.

SUMMARY OF THE INVENTION

The present invention is directed to a transmission type X-ray tube using filter materials to filter out unwanted radiation.

The present invention is directed to a reflection type X-ray tube using filter materials to filter out unwanted radiation.

The present invention provides a transmission type X-ray tube comprising a target material and a filter material. The target material comprises at least one element which generates X-rays including characteristic Kα and Kβ radiation energies of the element as being excited for producing images of an object impinged by the X-rays. The filter material through which the X-rays pass has a k-edge absorption energy that is higher than the Kα emission lines and lower than the Kβ emission lines of the element, and the thickness of the filter material is at least 10 microns and less than 3 millimeters.

In one embodiment of the present invention, the target material comprises elements, compounds, alloys, intermetallic compounds, or composite materials containing scandium, titanium, vanadium, chromium, manganese, iron, cobalt, nickel, copper, zinc, germanium, yttrium, niobium, molybdenum, ruthenium, rhodium, palladium, silver, tin, barium, lanthanum, cerium, neodymium, gadolinium, terbium, dysprosium, holmium, erbium, thulium, ytterbium, lutetium, hafnium, tantalum, tungsten, rhenium, iridium, platinum, gold, thorium or uranium or combinations thereof.

In one embodiment of the present invention, the filter material comprises elements, compounds, alloys, intermetallic compounds, or composite materials containing titanium, or yttrium, gadolinium, ruthenium, vanadium, samarium, neodymium, thorium, holmium, palladium, cobalt, cesium, niobium, tantalum, molybdenum, copper, chromium, iridium, erbium, rhodium, europium, indium, hafnium, rubidium, thulium, zinc, antimony, terbium, zirconium, manganese, nickel, rhenium, strontium, tungsten, nickel, cadmium, gallium, technetium, lutetium, dysprosium, iron, ytterbium or combinations thereof.

In one embodiment of the present invention, the target material has a thickness of 5 to 500 microns.

In one embodiment of the present invention, the transmission type x-ray tube is used as an x-ray source in an x-ray microscope.

In one embodiment of the present invention, the transmission type x-ray tube is used to obtain images for medical imaging.

The present invention provides a reflection type X-ray tube comprising a target material and a filter material. The target material comprises at least one element which generates X-rays including characteristic Kα and Kβ radiation energies of the element as being excited for producing images of an object impinged by the X-rays. The filter material through which the X-rays pass has a k-edge absorption energy that is higher than the Kα emission lines and lower than the Kβ emission lines of the element and the thickness of the filter material is at least 10 microns and less than 3 millimeters.

In one embodiment of the present invention, the target material comprises elements, compounds, alloys, intermetallic compounds, or composite materials containing scandium, titanium, vanadium, chromium, manganese, iron, cobalt, nickel, copper, zinc, germanium, yttrium, niobium, molybdenum, ruthenium, rhodium, palladium, silver, tin, barium, lanthanum, cerium, neodymium, gadolinium, terbium, dysprosium, holmium, erbium, thulium, ytterbium, lutetium, hafnium, tantalum, tungsten, rhenium, iridium, platinum, gold, thorium or uranium or combinations thereof.

In one embodiment of the present invention, the filter material comprises elements, compounds, alloys, intermetallic compounds, or composite materials containing titanium, or yttrium, gadolinium, ruthenium, vanadium, samarium, neodymium, thorium, holmium, palladium, cobalt, cesium, niobium, tantalum, molybdenum, copper, chromium, iridium, erbium, rhodium, europium, indium, hafnium, rubidium, thulium, zinc, antimony, terbium, zirconium, manganese, nickel, rhenium, strontium, tungsten, nickel, cadmium, gallium, technetium, lutetium, dysprosium, iron, ytterbium or combinations thereof.

In one embodiment of the present invention, the reflection type x-ray tube is used as an x-ray source in an x-ray microscope.

In one embodiment of the present invention, the reflection type x-ray tube is used to obtain images for medical imaging.

When an x-ray photon beam contains photons whose energies are just above the k-edge of a filtering material, that material strongly absorbs the given photon beam as is well known by those skilled in the art. If a filter substance can be found that has an absorption edge between the Kα and Kβ lines of the incident x-ray photon beam, this substance can be used to significantly reduce the intensity of the Kβ lines relative to the Kα lines and is defined as a Kβ filter.

The current invention discloses a transmission type x-ray tube designed with a target thickness of between 5 and 500 microns, which can be combined with Kβ filters chosen to provide filtering of both unwanted high energy to improve image quality and unwanted low energy x-rays to reduce patient dose in medical applications.

The current invention also discloses a reflection type x-ray tube used in medical imaging and in non-destructive test imaging and a filter designed to reduce the dose to considerably lower levels than is possible with low Z material filters such as aluminum or copper without decreasing significantly x-rays useful for imaging while at the same time decreasing high energy photons above the k-lines of the target material of the reflection type x-ray tube.

Thick transmission x-ray tube target materials and reflection type x-ray tube target materials are chosen from potential materials which include but are not limited to scandium, titanium, vanadium, chromium, manganese, iron, cobalt, nickel, copper, zinc, germanium, yttrium, niobium, molybdenum, ruthenium, rhodium, palladium, silver, tin, barium, lanthanum, cerium, neodymium, gadolinium, terbium, dysprosium, holmium, erbium, thulium, ytterbium, lutetium, hafnium, tantalum, tungsten, rhenium, iridium, platinum, gold, thorium or uranium.

The thickness of the chosen Kβ filter varies between about 10 microns and 3 millimeters in thickness.

The Kβ filters of the current invention are used to form both medical images including but not limited to patient breast, chest, joints and extremities, skull, abdomen, GI series, and images used to guide high energy radiation therapy to the precise location or locations inside the patient's body where such therapy is to be applied; and images for non-destructive testing wherein the object being imaged includes but is not limited to circuit boards, ball grid array circuits, discrete electronic components, micro-electro-mechanical systems (MEMS) devices, small animals, organic and geological samples, semiconductor chip packaging and many other inanimate objects used in various industries. The x-ray tubes and Kβ filters included have application as the x-ray source for an x-ray microscope in many non-destructive testing applications.

The present invention is directed toward imaging done with x-rays. Although it specifically solves significant problems in the field of medical imaging it also applies to all other kinds of x-ray imaging including non-destructive imaging of inanimate objects. It is applicable to x-ray imaging with both reflection x-ray type of tubes and transmission type x-ray tubes, solid target tubes as well as rotating anode tubes, and for all energies of x-rays used in medical and non-destructive test imaging. The invention introduces a way to reduce the x-radiation below and above a chosen useful x-ray energy band in the output spectrum of any x-ray tube. In x-ray applications which require a high concentration of monochromatic x-rays the current invention discloses ways to use a combination of thick transmission or reflection targets with a Kβ filter materials and thicknesses where the Kβ radiation of the x-ray target will be significantly reduced. One application x-ray tubes used with filters of the current invention is to provide quasi-monochromatic x-ray source for x-ray microscopes.

DESCRIPTION OF EMBODIMENTS

Figure 1:
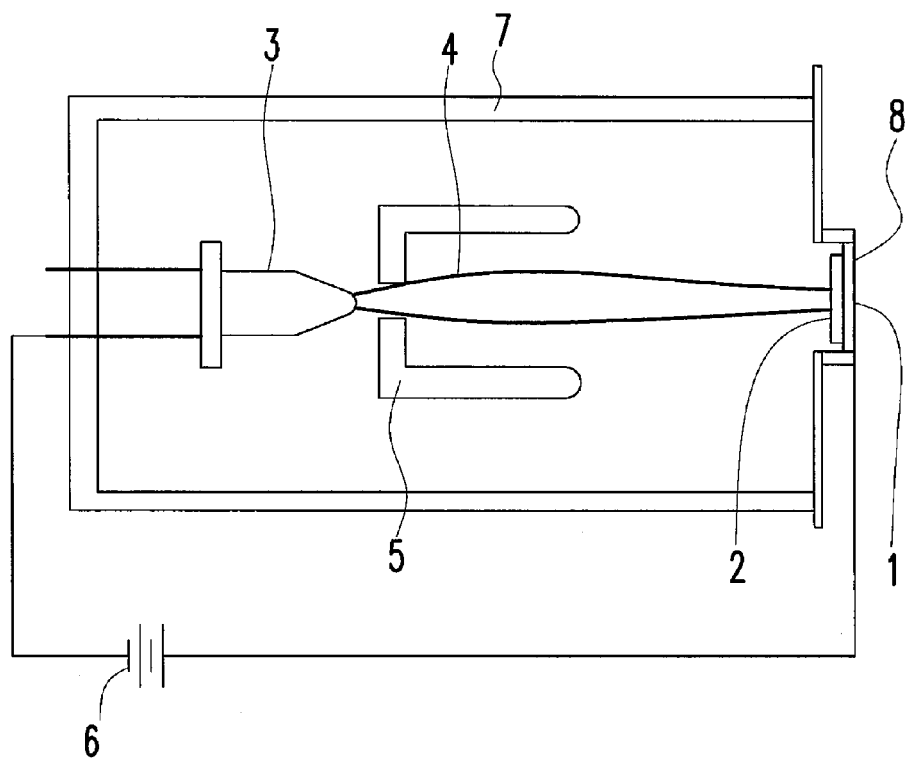
FIG. 1 is a schematic illustration of a transmission type x-ray tube which produces x-rays to be filtered by the current invention.

The transmission x-ray tube of FIG. 1 is comprised of an evacuated housing Item 7, and end-window anode 1 disposed at the end of the housing exposed to atmosphere. An x-ray target foil Item 2 is deposited onto the end-window anode Item 1. In some end-window x-ray tubes the x-ray target and the end-window are made of the same material, eliminating the need for a separate end-window material through which x-rays pass. When a thick target material is sufficiently strong to withhold the x-ray tube vacuum a separate end window material is not needed. An electrically or photon stimulated cathode Item 3 emits electrons, which are accelerated along the electron beam path Item 4 and strike the anode target producing x-rays Item 8. A power supply Item 6 is connected between the cathode and anode to provide the accelerating force for the electron beam. X-rays Item 8 produced exit the x-ray tube through the end-window. An optional focusing mechanism Item 5 typically electrically biased, focuses the electron beam above, below or onto a spot on the target. The largest dimension of the spot on the surface of the target is referred to as the focal spot size or spot size. The x-rays contain both Kα and Kβ characteristic radiation unique to at least one element in the target material. In one preferred embodiment of the current invention a transmission type x-ray tube with a target thickness as thin as 5 microns thick and as thick as 200 microns are deposited onto an end-window. When the target foil and the end window are of the same material the thickness can be as thick as 500 microns. In one preferred embodiment of the current invention the output of a transmission type x-ray tube is filtered through a Kβ filter with a filter thickness between 10 microns and 3 mm thick.

Figure 2:
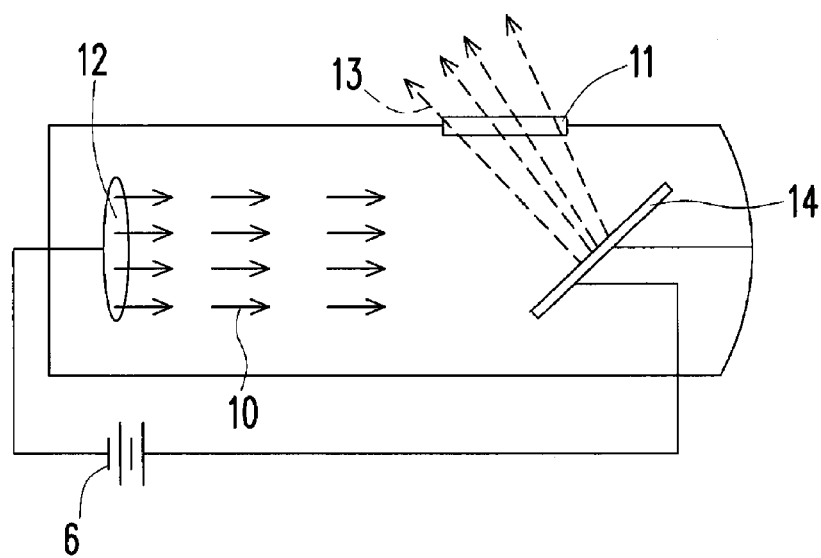
FIG. 2 is a schematic illustration of a reflection x-ray tube and its components which produces x-rays to be filtered by the current invention.

FIG. 2 schematically represents a reflection type x-ray tube comprised of an evacuated housing in which the cathode Item 12 and anode Item 14 are located. The anode Item 14 is comprised of an x-ray target deposited onto a substrate which substrate removes heat generated when x-rays impinge the anode. Electrons are emitted from the cathode in any way known to those skilled in the art. A power supply Item 6 is connected between the cathode and the anode to provide an electric field which accelerates the electrons from the cathode along an electron beam path 10 and strikes the anode Item 14 in a spot generating a beam of x-rays Item 13 which then exit the tube through a side window Item 11. The reflection tube harvests produced x-rays from the same side of the target that the electron beam impinges. The x-rays contain both Kα and Kβ characteristic radiation unique to at least one element in the target material useful in producing images of objects impinged by the x-rays produced. In one preferred embodiment of the current invention the output of a transmission type x-ray tube is filtered through a Kβ filter with a filter thickness between 10 microns and 3 mm thick.

Open transmission tubes are typically used for imaging of electronic circuits as well as other high-resolution applications and may alternatively be used as the x-ray source when high multiplication factors are required of the object's image. Closed tubes are sealed with a vacuum whereas open or "pumped down" tubes have a vacuum pump continuously attached drawing a vacuum as the tube is used usually to allow for frequent replacement of tube parts which tend to fail in operation. For purposes of this invention transmission tubes include both open and closed transmission type tubes except as otherwise stated.

Unless otherwise specified x-ray tube spectral data was taken with an Amptek Model XR-100 with a CdTe sensor 1 mm thick and 10 mils of Be filter. The sensor was placed at a distance of 1 meter from the x-ray tube and a tungsten collimator with a collimator hole of 100 μm diameter placed in front of the sensor. Various tube currents and exposure times were used.

Kβ filters are made of elements whose k absorption edge is located between the Kα lines and the Kβ lines of the x-ray target either in a transmission type x-ray tube or in a reflection type x-ray tube. Table 1 below illustrates for each possible target material used, the materials which form an appropriate Kβ filter of the current invention.

TABLE 1

Materials To Be Used for Kβ Filters of Transmission X-ray Tubes

| Possible Target Elements | Kα (1) | Filter Materials with their k-edge key |
|---|---|---|
| Vanadium | 4.9522 kev | Titanium 4.966 kev |
| Chromium | 5.4147 kev | Vanadium 5.4651 kev |
| Manganese | 5.8988 kev | Chromium 5.989 kev |
| Iron | 6.4038 kev | Manganese 6.539 kev |
| Cobalt | 6.9303 kev | Iron 7.112 kev |
| Nickel | 7.4781 kev | Cobalt 7.708 kev |
| Copper | 8.0478 kev | Nickel 8.333 kev |
| Zinc | 8.6389 kev | Copper 8.979 kev |
| Gallium | 9.2517 kev | Zinc 9.658 kev |
| Germanium | 9.886 kev | Gallium 10.367 kev |
| Yttrium | 14.958 kev | Strontium 16.105 kev<br>Rubidium 15.20 kev |
| Niobium | 16.615 kev | Yttrium 17.038 kev<br>Zirconium 17.998 kev |
| Molybdenum | 17.479 kev | Niobium 18.986 kev<br>Zirconium 17.998 kev |
| Ruthenium | 19.279 kev | Molybdenum 19.999 kev<br>Technetium 21.004 kev |
| Rhodium | 20.216 kev | Ruthenium 22.117 kev<br>Technetium 21.044 kev |
| Palladium | 21.177 kev | Rhodium 23.220 kev<br>Ruthenium 22.117 kev |
| Silver | 22.163 kev | Palladium 24.350 kev<br>Rhodium 23.220 kev |
| Tin | 25.271 kev | Indium 27.940 kev |
| Antimony | 26.359 kev | Tin 29.200 kev<br>Cadmium 26.711 kev |
| Tellurium | 27.472 kev | Antimony 30.491 kev<br>Tin 29.200 kev |
| Lanthanum | 33.442 kev | Cesium 35.985 kev |
| Gadolinium | 42.996 kev | Samarium 46.834 kev<br>Neodymium 43.569 |
| Terbium | 44.481 kev | Europium 48.519 kev<br>Samarium 46.834 kev |
| Dysprosium | 45.998 kev | Gadolinium 48.697 kev.<br>Terbium 51.966 kev. |

TABLE 1-continued

Materials To Be Used for Kβ Filters of Transmission X-ray Tubes

| Possible Target Elements | Kα (1) | Filter Materials with their k-edge key |
|---|---|---|
| Holmium | 47.547 kev | Samarium 46.834 kev<br>Dysprosium 53.778 kev<br>Gadolinium 48.697 kev. |
| Erbium | 49.128 kev | Terbium 51.966 kev.<br>Holmium 55.617 kev<br>Dysprosium 53.778 kev |
| Thulium | 50.742 kev | Terbium 51.996 kev<br>Gadolinium 50.239 kev<br>Erbium 57.485 kev<br>Holmium 55.617 kev<br>Dysprosium 53.778 kev<br>Terbium/51.996 kev |
| Ytterbium | 52.389 kev | Erbium 57.485 kev<br>Holmium 55.617 kev<br>Dysprosium 53.778 kev |
| Lutetium | 54.069 kev | Only relatively stable in air.<br>Thulium 59.390<br>Erbium 57.485 kev<br>Holmium 55.617 kev |
| Hafnium | 55.790 kev | Ytterbium 61.332 kev<br>Thulium 59.390 kev<br>Erbium 57.485 kev |
| Tantalum | 57.532 kev | Lutetium 63.314 kev<br>Ytterbium 61.332 kev<br>Thulium 59.390 kev |
| Tungsten | 59.318 kev | Hafnium 65.351 kev<br>Lutetium 63.314 kev<br>Ytterbium 61.332 kev<br>Thulium 59.390 kev |
| Rhenium | 61.140 kev | Tantalum 67.416 kev<br>Hafnium 65.351 kev<br>Lutetium 63.314 kev |
| Iridium | 64.896 kev | Tungsten 69.525 kev<br>Tantalum 67.416 kev<br>Hafnium 65.351 kev |
| Platinum | 66.832 kev | Rhenium 71.676 kev<br>Tungsten 69.525 kev<br>Tantalum 67.416 kev |
| Gold | 68.804 kev | Iridium 76.111 kev<br>Rhenium 71.676 kev<br>Tungsten 69.525 kev |
| Uranium | 98.439 kev | Thorium 109.65 kev |

Figure 3:
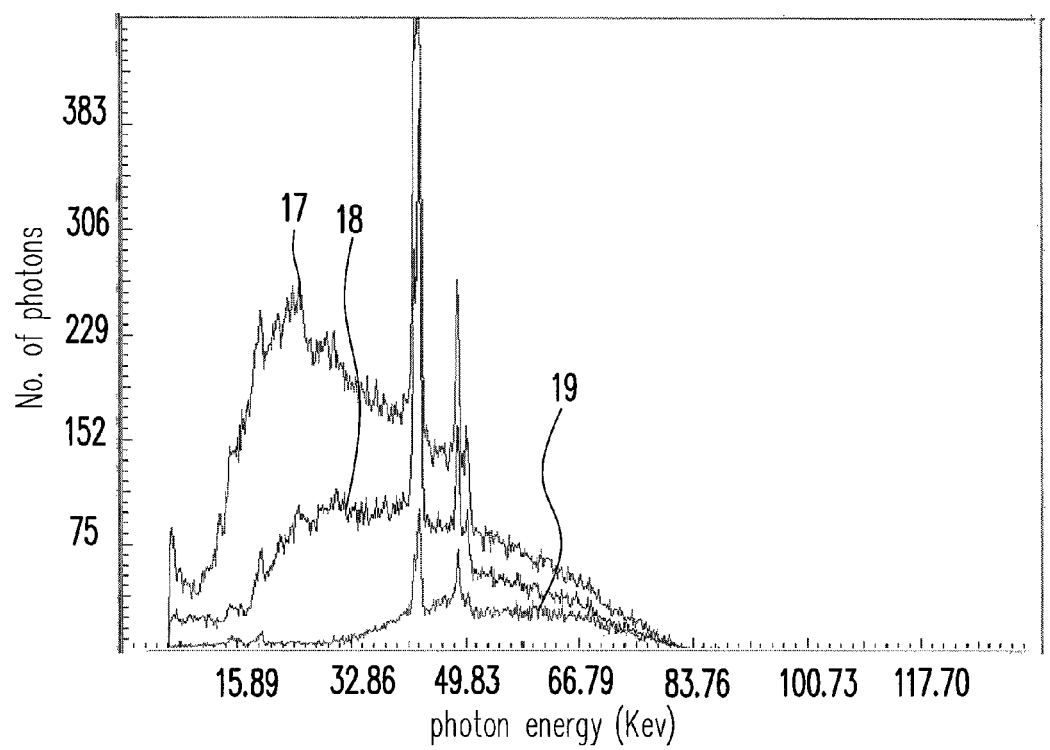
FIG. 3 is a graphical representation of the output spectrum from a transmission x-ray tube with a gadolinium target filtered through aluminum and copper.

FIG. 3 represents the output of a transmission type of x-ray tube with a gadolinium target 20 microns thick. The applied voltage of this tube is 80 kVp. Item 17 represents the output spectrum of the tube with no filtering except the self filtering of the thick gadolinium target. Although a target thickness of 20 microns was used the target thickness can range from less than 5 microns thick to many hundreds of microns. Item 18 represents the output spectrum of the same x-ray tube filtered through a low Z aluminum filter 1.5 mm thick. Item 19 represents the output spectrum filtered through an aluminum equivalent thickness of 9 mm. Filtering the gadolinium with traditional low Z filtering schemes will not provide low dose and at the same time sufficient flux to use with image contrast agents such as iodine or barium.

Figure 4:
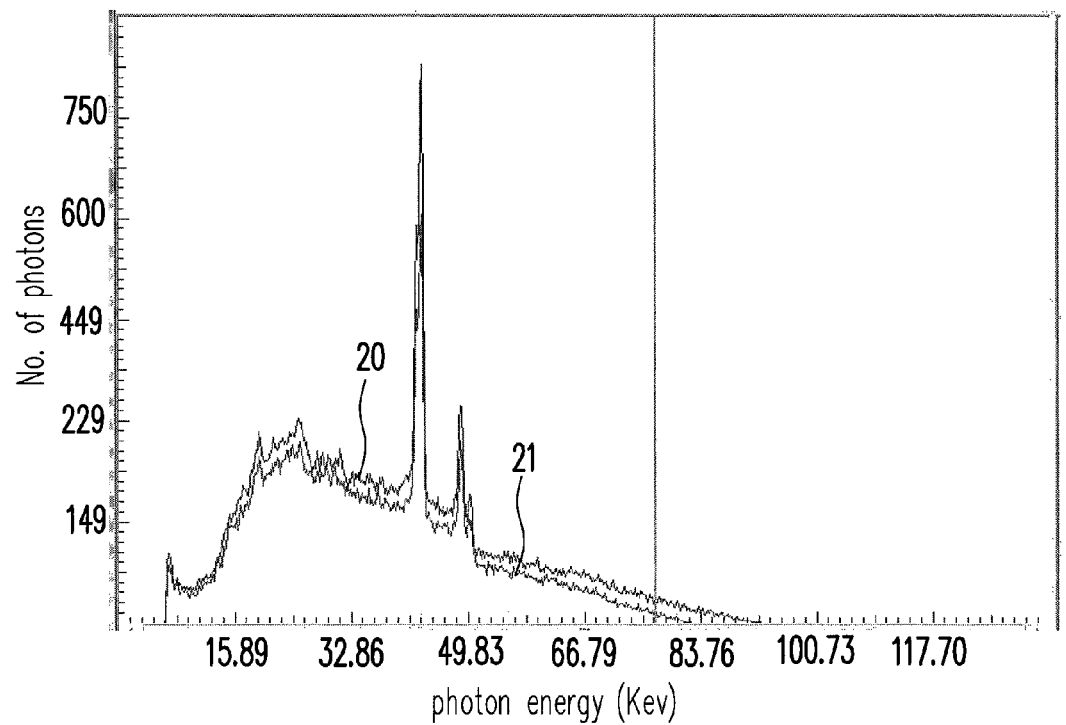
FIG. 4 is a graphical representation of the output spectrum of a transmission tube with a gadolinium target 20 microns thick and no filtering.

FIG. 4 represents the x-ray output spectrum from a transmission type x-ray tube with a target of Gadolinium 20 microns thick at 80 kVp (Item 20) and 90 kVp (Item 21) applied tube voltage with no filtering except the self filtering of the thick transmission target. Gadolinium can be used to image barium since the mass absorption coefficient of barium at 42.7 (the Kα of gadolinium) kev is 22.4 $cm^2/gm$. It can also be used to image the imaging agent iodine which has a mass absorption coefficient of 18.46 $cm^2/gm$ at 42.7 kev. Gadolinium is a very suitable source of Kα radiation to provide significant contrast from any barium and iodine imaging agent in the image to be taken. By increasing the thickness of the gadolinium target, additional self filtering of the output spectrum can be accomplished with little decrease in the useful flux at 42.7 kev.

Figure 5:
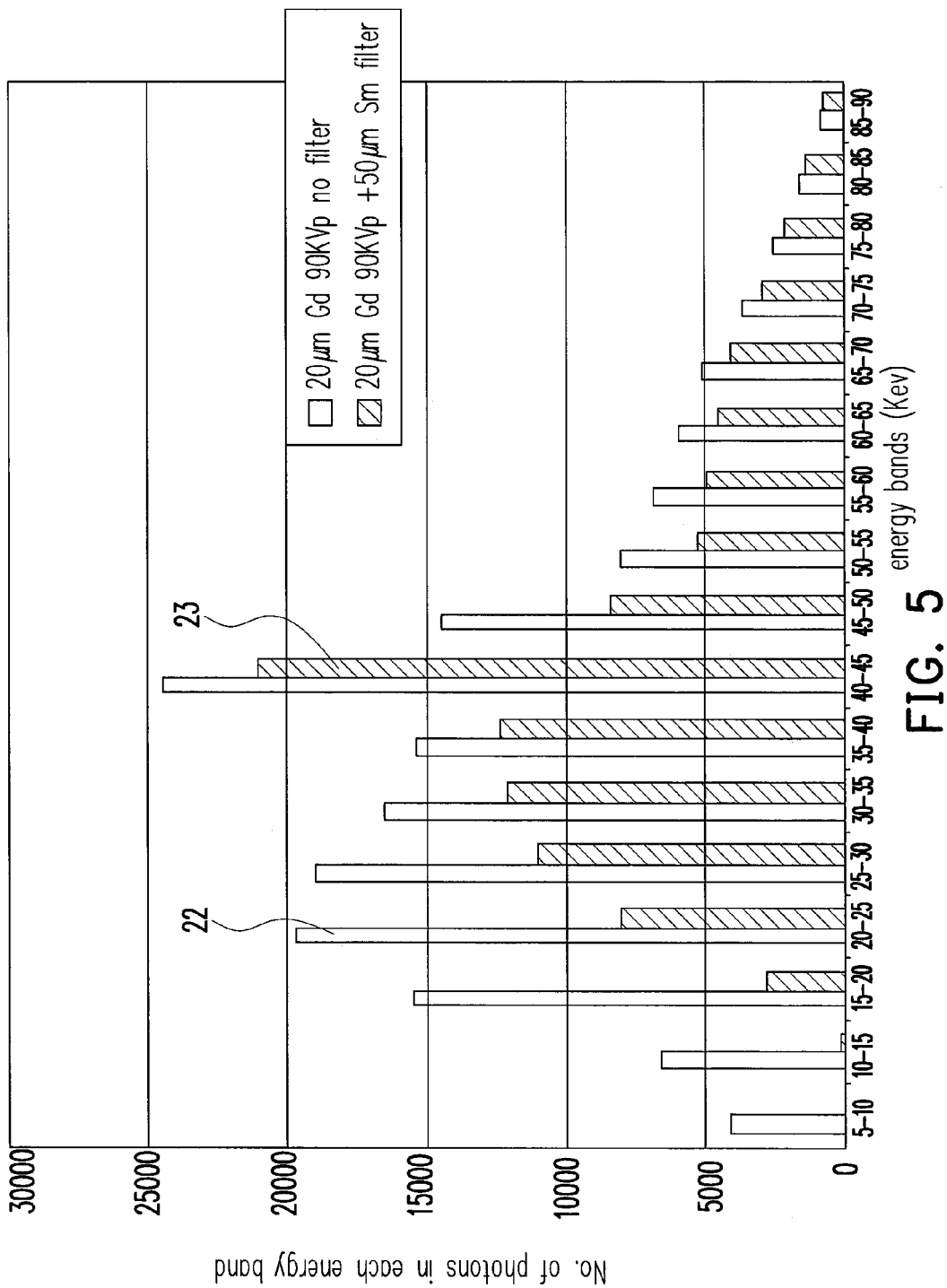
FIG. 5 is a graphical representation of the output spectrum of a transmission x-ray tube with a gadolinium target and a filter of samarium.

FIG. 5 illustrates one preferred embodiment of the current invention. From Table 1 samarium is seen as one of two Kβ filter materials for gadolinium. A thickness of 50 microns of samarium is used to filter the output of the above described 20 micron thick gadolinium transmission type x-ray tube target. The samarium filter is mathematically applied to the gadolinium output at 90 kVp and represented in FIG. 5. Item 22 shows the spectrum of the gadolinium target at 90 kVp with no filtering. Item 23 illustrates how the Kβ filter of 50 microns of samarium decreases the counts in each energy band. The Kα band of gadolinium was reduced only about 10% whereas energy in the 45 to 50 kev (Kβ of gadolinium is 48.69) energy band were reduced almost 40%. There is a 58% decrease in the photon counts below 35 kev photon energy, a significant decrease in patient dose and a 30% decrease in the output energy from 45kev to 90 kev reducing the amount of contrast degradation attributed to high energy photons not useful in creating the image. Although a gadolinium target thickness of 20 microns was used as an example here, a target thickness from as thin as 5 microns to as thick as 200 microns could alternatively be used. The thickness of the filter could be decreased to 10 microns with resultant decreased filtering and stronger Kα output or it could be as thick as 3 millimeters if the gadolinium target is 100 micron thick or thicker and the accelerating voltage of the tube is as high as 150 kVp.

Figure 6:
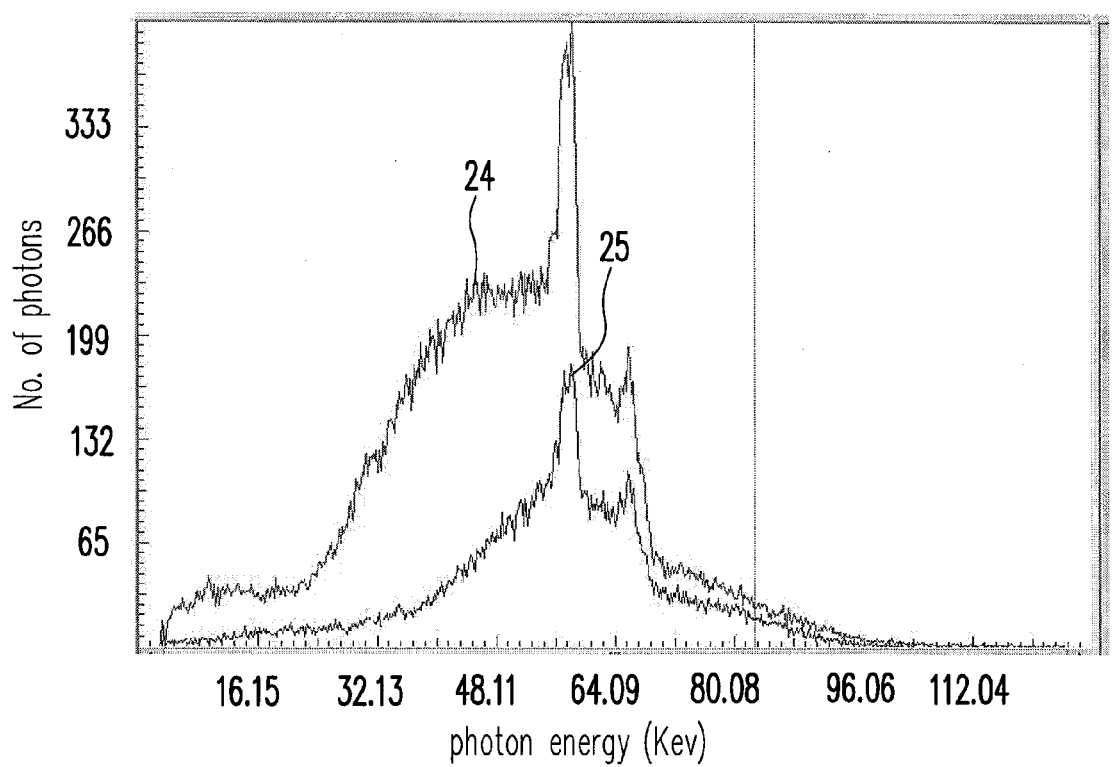
FIG. 6 is a graphical representation of the spectrum of a transmission x-ray tube with a thick tantalum target filtered with traditional low Z materials.

FIG. 6 is a graphical representation of the output spectrum of a transmission tube with a 75 micron thick target material of tantalum operated at 50 microamps of tube current with a 9 mm equivalent aluminum filter typically used in medical imaging. Item 24 represents the unfiltered output. Item 25 represents the output when filtered through a low Z filter with the 9 mm equivalent aluminum filter. In the low energy photon band from 0 to 40 kev there is a decrease of 60.5% x-ray counts significantly reducing unwanted low energy x-rays from causing radiation harm to the patient. At the same time however, the useful x-rays in the range of 40 to 70 kev are reduced by 60%. X-rays above 70 kev, chosen to represent those x-rays which detract from image contrast, are decreased by 26.7%. However, compared to the decrease of 60% of useful x-rays there are proportionately higher amounts of high energy x-rays. The increase is from 12.2% for the unfiltered output to 19.3% for the filtered. Hence while the low Z filter effectively decreases the dose to the patient, it also reduces a high percentage of the useful x-rays as well. The effect of the high energy photons about 70 kev are worsened by using the filter.

It should be noted that a transmission type x-ray tube with a 75 micron thick transmission target already has significant reduction of the low energy by the self filtering of x-rays which must pass through the thick target before exiting the end window.

Although comparison of x-ray photon energies was made for energies <40 kev there are applications where x-rays in the range of 30 to 40 kev are very important to obtaining a quality image. Likewise 40 to 70 kev x-ray of useful x-ray energies were chosen arbitrarily to demonstrate the concepts of the current invention. Each imaging application for either medical or non-destructive testing will have its own definition of useful and non-useful x-ray radiation. Then filtering technology of the current invention will be used to optimize the useful x-rays within limits of allowed tube current while reducing unwanted x-ray photons which do not contribute to x-ray image quality.

Figure 7:
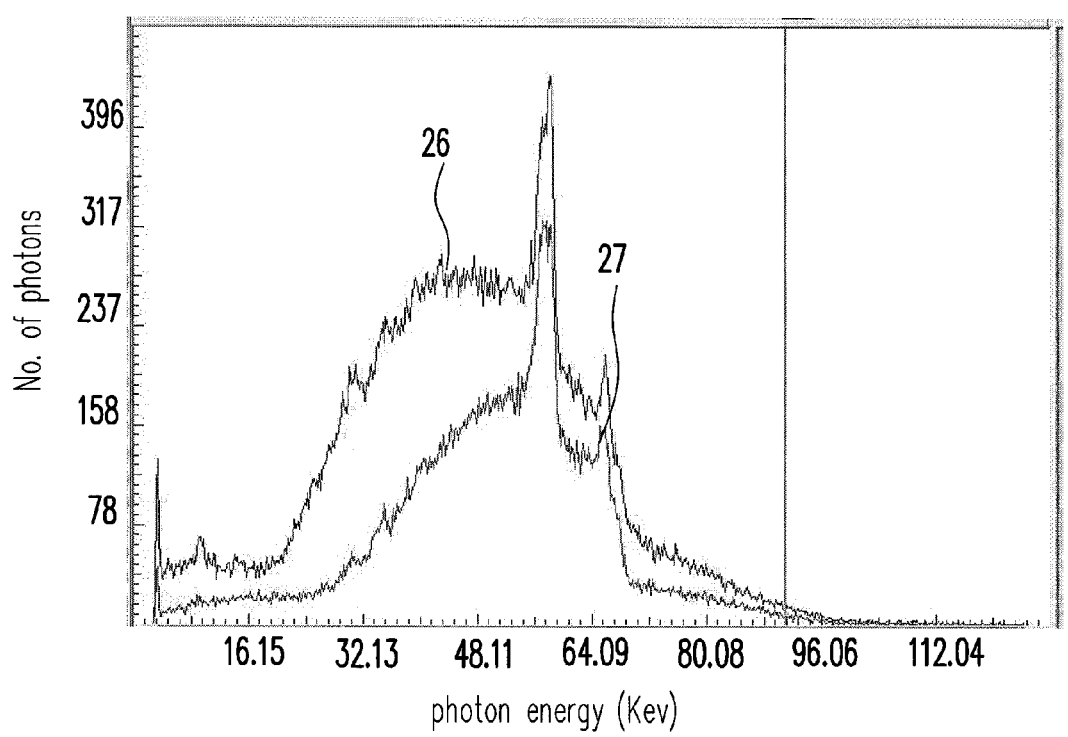
FIG. 7 is a graphical representation of the spectrum of a 50 micron thick tantalum transmission target and a 100 micron thick tantalum target with no filtering.

FIG. 7 illustrates the self-filtering feature of a transmission tube with a thick target foil. Item 26 represents the spectrum of a transmission tube having a target thickness of 50 microns. Item 27 represents the spectrum of a transmission tube having a target thickness of 100 microns. Both tubes are operated at 100 kVp tube voltage and a tube current of 50 µA tube current. Table 2 below summarizes the number of photon counts for each tube in the energy bands of <40 kev, from 40 to 70 kev, and from 70 to 100 kev.

TABLE 2

| Target Thickness | Counts <40 kev | Counts 40-70 kev | Counts 70-100 kev |
|---|---|---|---|
| 50 microns Ta | 64,865 | 117,106 | 14,888 |
| 100 microns Ta | 21,482 (−72%) | 76,707 (−34.5%) | 7,623 (−48.8%) |

Whereas the reduction in useful x-rays in the energy band between 40 and 70kev is about 34.5%, the x-rays below 40 kev considered to add to the patient dose is reduced by 72%. Additionally the reduction of x-rays in the energy band 70 to 100 kev is 48.8% considerably more that the loss of useful x-rays.

Figure 8:
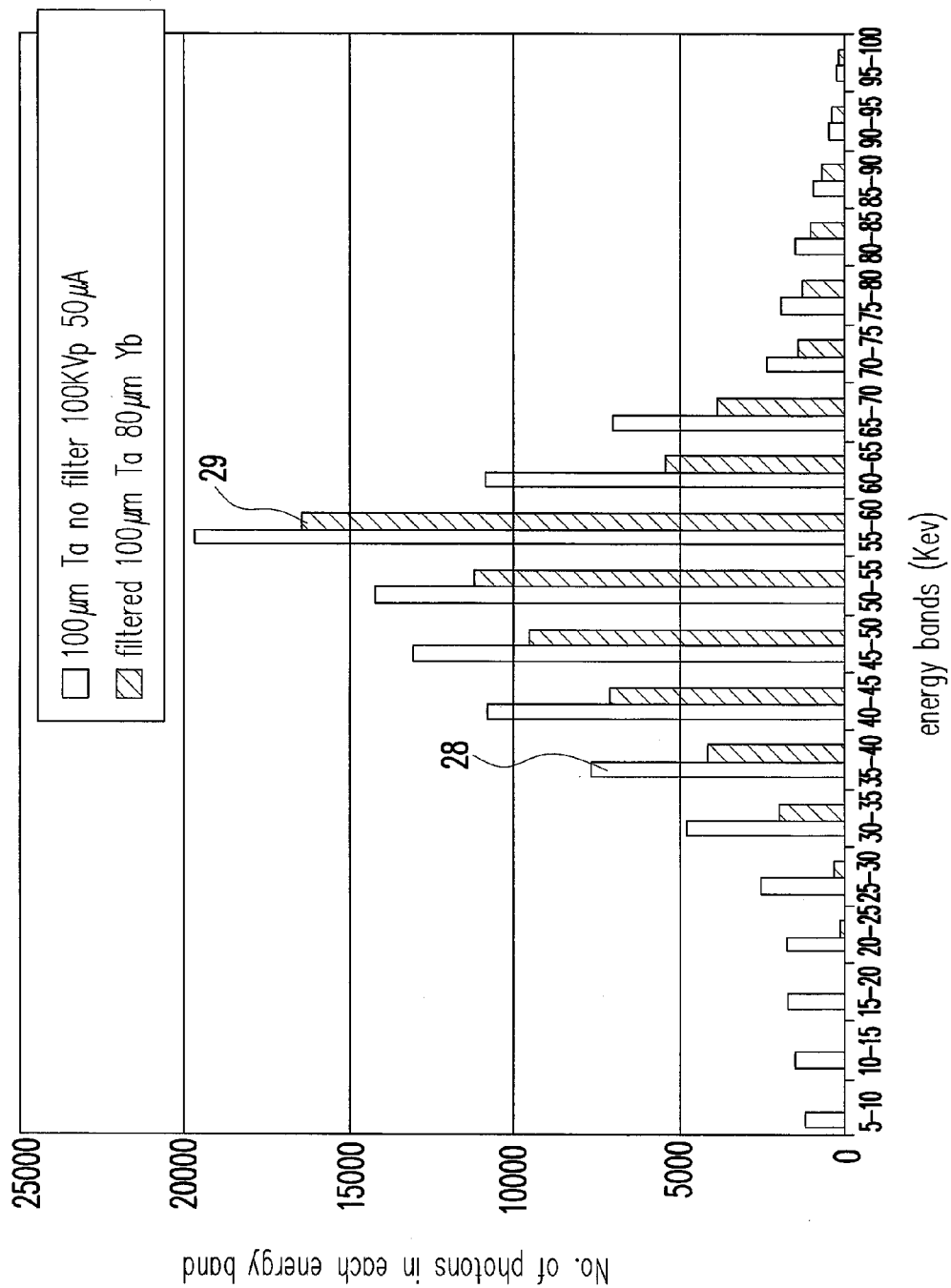
FIG. 8 is a graphical representation of the output spectrum of a transmission x-ray tube with a tantalum target 100 microns thick and a filter of ytterbium 80 microns thick.

In one preferred embodiment of the current invention, an additional filter is added to the already existent self-filtering of the 100 micron thick target. The filter material chosen from Table 1 can be one of lutetium, thulium or ytterbium. FIG. 8 represents the number of counts of photons in each energy band for a spectrum of a transmission x-ray tube with a tantalum target 100 microns thick operated at 100 kVp tube voltage and a tube current of 50 microamps. Item 28 represents the data taken when no additional filter is used and Item 29 is a graphical representation of the calculated filtered output that will be obtained with an ytterbium filter 80 microns thick. Table 3 below summarizes the difference in the two spectrum.

TABLE 3

| Target Thickness | Counts <40 kev | Counts 40-70 kev | Counts 70-100 kev |
|---|---|---|---|
| 100 Ta no Filter | 21255 | 75851 | 7540 |
| 100 Ta 80 mm Yb Filter | 6655 (−68.7%) | 53618 (−29.4%) | 5084 (−33%) |

There is an additional 68.7% reduction in the amount of unwanted x-rays below 40 kev which translates to a reduction in harmful dose to the patient. This reduction comes at the expense of reduced counts in the 40 to 70 kev useful x-ray range of 29.4% but the percentage reduction in useful x-rays is considerably smaller than the percentage reduction in dose below 40 kev. In the energies higher than 70 kev there is a net loss in total counts as a result of the ytterbium filter compared to the loss of useful x-rays. Not shown in FIG. 8 is the addition to useful x-rays contributed when the absorbed energies above 61.332 kev (k-edge of ytterbium) are converted to Kα x-rays of ytterbium with a Kα of 52.4 kev when the ytterbium atoms fluoresce. The 80 micron thick ytterbium filter is used with a 100 micron thick tantalum target at 100 kVp only as a way to explain the filtering principle which could have used different filtering materials, different x-ray tube voltages, different filter thickness, different transmission target thickness and different transmission target materials to develop a filtering scheme considerably superior to using low Z materials such as copper and aluminum to filter for x-ray imaging.

When inanimate objects are being imaged with x-rays of the current invention, more emphasis is placed on providing less x-ray energy above the x-rays needed to produce a high quality image. Those higher energies currently only reduce image contrast.

In another preferred embodiment of the current invention output from a reflection tube with a tungsten target material and filtered with traditional low Z materials of copper and aluminum. The use of high Z filters of an atomic number lower than but close to that of the target material is described provides considerably more efficient filtering resulting in low dose with minimal loss of useful radiation.

Figure 9:
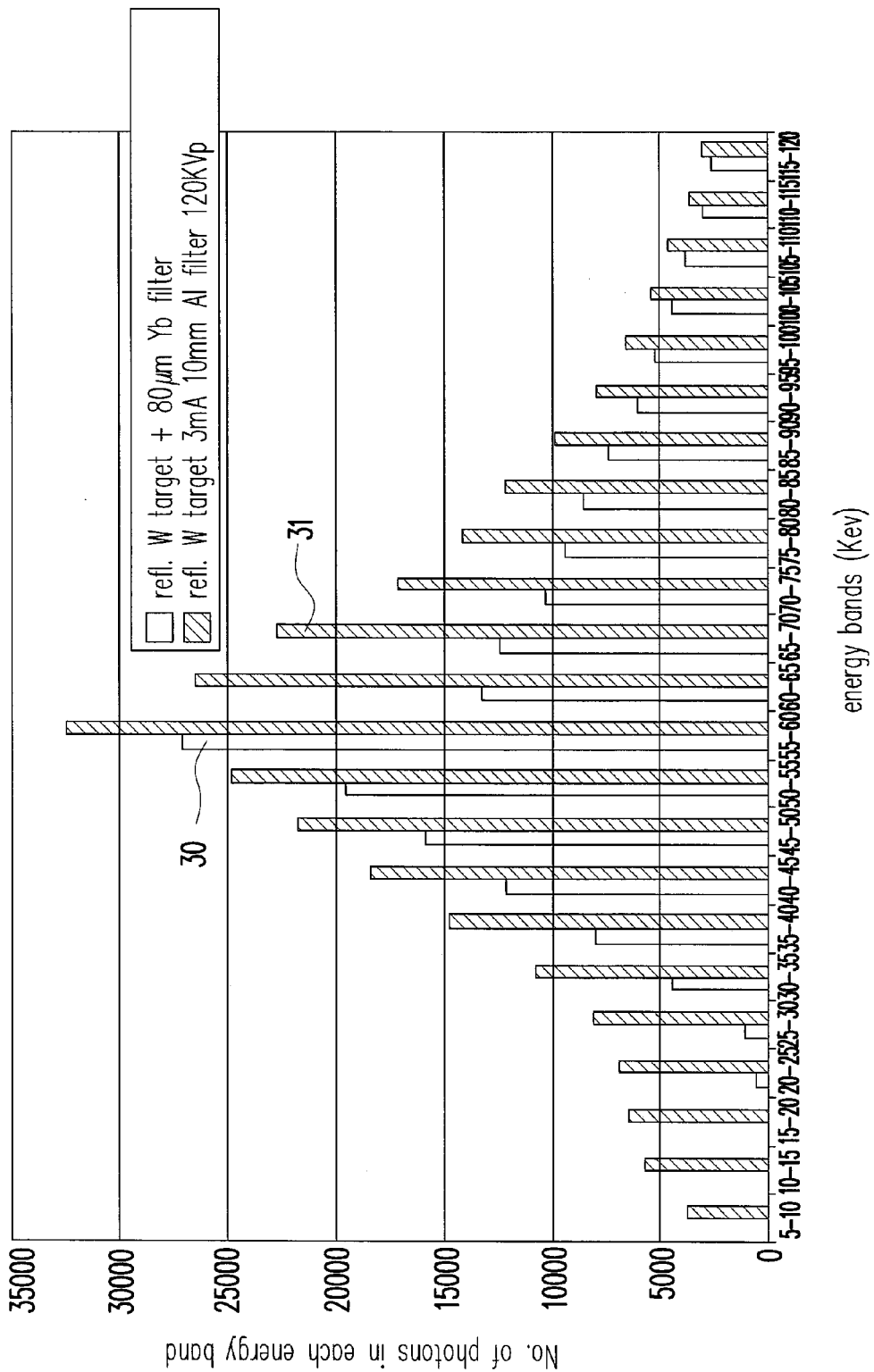
FIG. 9 is a graphical representation of the output spectrum of a reflection tube filtered by standard low Z filter materials compared to adding a 80 micron ytterbium filter.

FIG. 9 is a representation of the distribution of x-ray flux output from a traditional reflection tube. Item 31 represents the spectrum from a reflection tube with a tungsten target operated at 120 kVp tube voltage and a tube current of 3 mA. The output has been filtered through a traditional "low Z" filter of an equivalent 9 mm of aluminum. Item 30 shows the calculated results of further filtering the output with a filter of the current invention. From Table 1 filter materials for tungsten include hafnium, lutetium, ytterbium and thulium. Ytterbium was chosen with a filter thickness of 80 microns. Choosing a target material from Table 1 with a Z higher than ytterbium would shift the output to a higher energy output, well understood by anyone skilled in the art.

Table 4 below shows clearly that there is an additional reduction of photons with energies less than 40 kVp of 74.8% considerably reducing the amount of x-ray dose experienced by the patient with a reduction of only 38% in useful x-rays. Although this data uses both a combination of low Z filtering and filtering technology of the current invention, the low Z filtering can be replaced with a filter of the current invention with considerable efficiency improvement. The filter will emit its own k-line fluorescent emissions not included in FIG. 9 which will only increase the total output amount of photons in the useful range of 40 to 70 kev and reduce the amount of tube current to obtain the same quality image.

TABLE 4

| Target Thickness | Counts <40 kev | Counts 40-70 kev | Counts 70-100 kev |
|---|---|---|---|
| Tungsten Reflection Tube at 120 kVp and 9 mm Al Filter | 56481 | 161589 | 67369 |
| Tube above w/80 mm Yb Filter | 14266 (−74.8%) | 100249 (−38%) | 50442 (−25%) |

In one preferred embodiment a Kβ filter matched to target materials of either transmission type x-ray tubes or reflection type x-ray tubes is used as an x-ray source for medical imaging including but not limited to imaging of patient breasts, chests, joints and extremities, skulls, abdomens, GI series, and images used to guide high energy radiation therapy to the precise location or locations inside the patient's body where such therapy is to be applied.

In another preferred embodiment of the current invention a Kβ filter matched to target materials of either transmission type x-ray tubes or reflection type x-ray tubes as a quasi-monochromatic x-ray source in non-destructive imaging of materials and biological samples including but not limited to circuit boards, ball grid array circuits, discrete electronic components, micro-electro-mechanical systems (MEMS) devices, LED's, lithium batteries, small animals, organic and geological samples, semiconductor chip packaging and many other inanimate objects used in various industries. Applications are many and include use as the x-ray source for x-ray microscopes.

Figure 10:
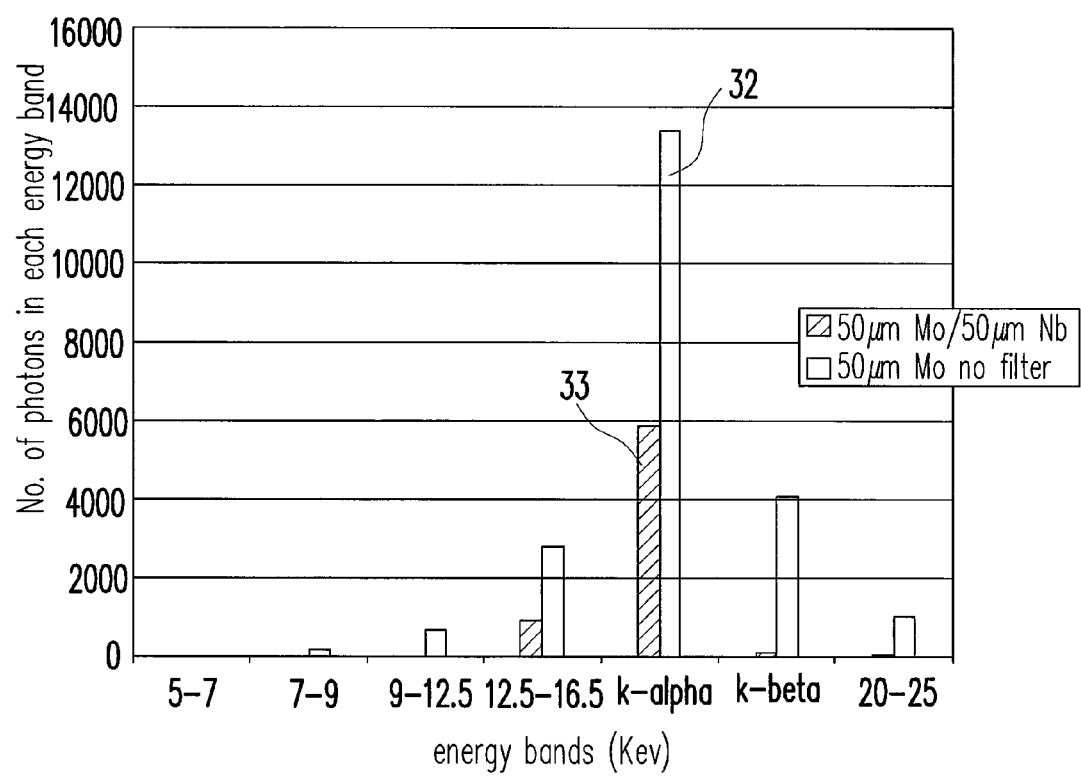
FIG. 10 is a graphical representation of filtering the output from a molybdenum target transmission x-ray tube with niobium filter.

FIG. 10 represents one embodiment of the current invention. A transmission x-ray tube with a thick molybdenum target of 50 microns was measured with a tube voltage of 60kVp. With no additional filtering, the spectrum of the molybdenum x-ray tube, Item 32, contained 13,409 Kα photons and the number of Kβ photons was 4,076. When an additional 50 micron thick niobium filter chose from Table 1 as a Kβ filter is added there is a calculated decease in Ka radiation to 5,862 whereas the Kβ radiation decreased to 98 counts. Using the thick molybdenum transmission tube and a 50 micron thick niobium Kβ filter, the Kα radiation was reduced, Item 33, by a factor of 2.2 while the Kβ radiation was reduced by a factor of 41.6.

For the entire energy band from 20 to 25 kev, item 32 had only 37 photon counts. This represents a very high level of monochromatic Kα radiation from a molybdenum tube. Although molybdenum and niobium were used to provide an example any of the other target materials and Kβ filter materials of Table 1 could be used as well.

Figure 11:
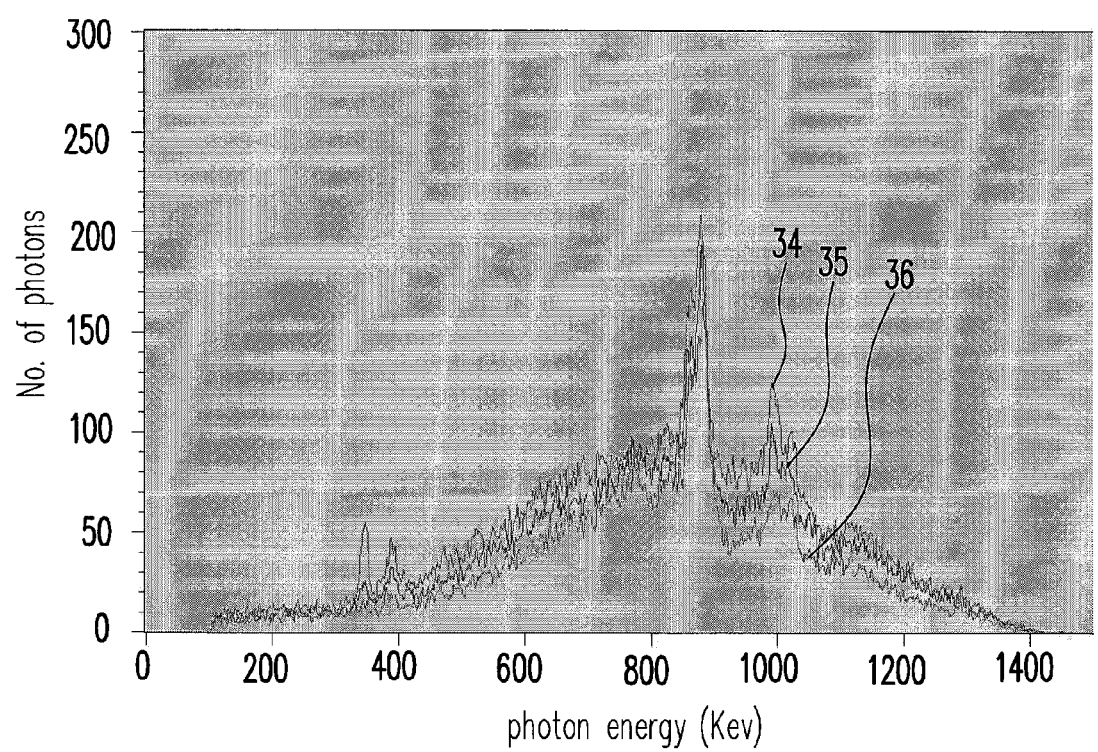
FIG. 11 is a graphical representation of the output flux from a transmission x-ray tube of the current invention using a filter made of thulium in three different thicknesses and the transmission x-ray tube of the current invention has a tantalum target.

FIG. 11 is a graphical representation of the output flux from a transmission x-ray tube of the current invention with a tantalum target 50 microns thick and three different k-beta filters of the current invention made of thulium applied to the output. The voltage applied to the tube is 90 kVp and the tube current is 50 microamps. The spectrum are measured after filters are applied. The three filters were 25 microns, Item 34, 50 microns, Item 35, and 75 microns, Item 36, thick. Table 5 below describes amount of useful k-alpha filtered compared to the decrease of unwanted k-beta flux and also to the amount of low energy photons comprising mostly dose with no use in imaging from 15 kev to 40 kev.

TABLE 5

| Thulium filter Thickness | k-alpha 54.7-58.2 kev | k-beta 63.6-66.9 kev | Low Energy 15-40 kev |
| --- | --- | --- | --- |
| 25 microns | 8067 counts | 5134 counts | 12,587 counts |
| 50 microns | 7198 counts | 4054 counts | 9,670 counts |
| 75 microns | 6285 counts −22.1% | 3090 counts −39.8% | 7,145 counts −43.3% |

It is demonstrated that as the thulium filter is increased in thickness from 25 microns to 75 microns there is decrease useful k-alpha emission by only about 22% compared to a decrease in unwanted k-beta of about 40% and a decrease in unwanted low energy from 15 kev to 40 kev of about 43%. The desired decrease in low energy photon and high k-beta photons is accomplished with a single filter of the current invention provide a significant improvement in the dose that a patient would see. The thickness used here is for illustrative purposes only. It is clear that filters of any thickness could be used with varying effectiveness. Any decrease in the useful x-rays could be offset by increasing the tube current. There is a limit to the amount of tube current increase that can be allowed depending on the total energy impinging the focal spot on the target of the transmission x-ray tube.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A transmission type X-ray tube, comprising:
   a target material comprising at least one element which generates X-rays including characteristic Kα and Kβ radiation energies of the element as being excited for producing images of an object impinged by the X-rays; and
   a filter material through which the X-rays pass having a k-edge absorption energy that is higher than the Kα emission lines and lower than the Kβ emission lines of the element;
   wherein the thickness of the filter material is at least 10 microns and less than 3 millimeters,
   wherein the target material is different from the filter material and has a thickness of 5 to 500 microns.

2. The transmission type x-ray tube of claim 1, wherein the target material comprises elements, compounds, alloys, intermetallic compounds, or composite materials containing scandium, titanium, vanadium, chromium, manganese, iron, cobalt, nickel, copper, zinc, germanium, yttrium, niobium, molybdenum, ruthenium, rhodium, palladium, silver, tin, barium, lanthanum, cerium, neodymium, gadolinium, terbium, dysprosium, holmium, erbium, thulium, ytterbium, lutetium, hafnium, tantalum, tungsten, rhenium, iridium, platinum, gold, thorium or uranium or combinations thereof.

3. The transmission type x-ray tube of claim 1, wherein the filter material comprises elements, compounds, alloys, intermetallic compounds, or composite materials containing titanium, or yttrium, gadolinium, ruthenium, vanadium, samarium, neodymium, thorium, holmium, palladium, cobalt, cesium, niobium, tantalum, molybdenum, copper, chromium, iridium, erbium, rhodium, europium, indium, hafnium, rubidium, thulium, zinc, antimony, terbium, zirconium, manganese, nickel, rhenium, strontium, tungsten, nickel, cadmium, gallium, technetium, lutetium, dysprosium, iron, ytterbium or combinations thereof.

4. A reflection type X-ray tube, comprising:
   a target material comprising at least one element which generates X-rays including characteristic Kα and Kβ radiation energies of the element as being excited for producing images of an object impinged by the X-rays; and
   a filter material through which the X-rays pass having a k-edge absorption energy that is higher than the Kα emission lines and lower than the Kβ emission lines of the element;
   wherein the thickness of the filter material is at least 10 microns and less than 3 millimeters,
   wherein the target material is different from the filter material and has a thickness of 5 to 500 microns.

5. The reflection type x-ray tube of claim 4, wherein the target material comprises elements, compounds, alloys, intermetallic compounds, or composite materials containing scandium, titanium, vanadium, chromium, manganese, iron, cobalt, nickel, copper, zinc, germanium, yttrium, niobium, molybdenum, ruthenium, rhodium, palladium, silver, tin, barium, lanthanum, cerium, neodymium, gadolinium, terbium, dysprosium, holmium, erbium, thulium, ytterbium, lutetium, hafnium, tantalum, tungsten, rhenium, iridium, platinum, gold, thorium or uranium or combinations thereof.

6. The reflection type x-ray tube of claim 4, wherein the filter material comprises elements, compounds, alloys, intermetallic compounds, or composite materials containing titanium, or yttrium, gadolinium, ruthenium, vanadium, samarium, neodymium, thorium, holmium, palladium, cobalt, cesium, niobium, tantalum, molybdenum, copper, chromium, iridium, erbium, rhodium, europium, indium, hafnium, rubidium, thulium, zinc, antimony, terbium, zirconium, manganese, nickel, rhenium, strontium, tungsten, nickel, cadmium, gallium, technetium, lutetium, dysprosium, iron, ytterbium or combinations thereof.

* * * * *